United States Patent
Nakagawa et al.

(10) Patent No.: US 7,502,438 B2
(45) Date of Patent: Mar. 10, 2009

(54) X-RAY CT APPARATUS AND MEDICAL DATA COMMUNICATION LINK SYSTEM

(75) Inventors: Shouichi Nakagawa, Otawara (JP); Michihiro Yamashita, Nasushiobara (JP)

(73) Assignees: Kabushiki Kaisha Toshiba, Tokyo (JP); Toshiba Medical Sstems Corporation, Otawara-shi (JP)

( * ) Notice: Subject to any disclaimer, the term of this patent is extended or adjusted under 35 U.S.C. 154(b) by 75 days.

(21) Appl. No.: 11/623,991

(22) Filed: Jan. 17, 2007

(65) Prior Publication Data

US 2007/0165776 A1 Jul. 19, 2007

(30) Foreign Application Priority Data

Jan. 18, 2006 (JP) ............................. 2006-010055

(51) Int. Cl.
*H05G 1/08* (2006.01)
*H05G 1/60* (2006.01)

(52) U.S. Cl. .......................................... 378/15; 378/91

(58) Field of Classification Search .................. 378/4, 378/15, 19, 91
See application file for complete search history.

(56) References Cited

U.S. PATENT DOCUMENTS

| | | | |
|---|---|---|---|
| 5,010,254 A | | 4/1991 | Moore |
| 5,018,174 A | * | 5/1991 | Collins .......................... 378/4 |
| 5,134,639 A | | 7/1992 | Vekstein et al. |
| 5,140,696 A | * | 8/1992 | Fox ............................. 455/41.1 |
| 5,157,393 A | * | 10/1992 | Fox et al. .................. 340/870.3 |
| 5,208,581 A | * | 5/1993 | Collins ....................... 340/671 |
| 5,336,897 A | | 8/1994 | Watanabe et al. |
| 5,530,424 A | | 6/1996 | Harrison et al. |
| 5,579,357 A | * | 11/1996 | Harrison ......................... 378/4 |
| 6,181,766 B1 | * | 1/2001 | Pearson et al. ................ 378/15 |
| 6,292,919 B1 | * | 9/2001 | Fries et al. ................... 714/758 |
| 6,301,324 B1 | * | 10/2001 | Pearson et al. ................ 378/15 |
| 6,327,327 B1 | * | 12/2001 | Herold et al. .................. 378/15 |
| 6,580,853 B2 | * | 6/2003 | Harrison et al. ............... 385/31 |
| 6,862,299 B2 | * | 3/2005 | Popescu ...................... 370/516 |
| 6,914,957 B2 | * | 7/2005 | Dafni et al. ................... 378/15 |
| 6,980,714 B2 | * | 12/2005 | Lo et al. ....................... 385/26 |
| 7,079,619 B2 | * | 7/2006 | Katcha et al. ................. 378/15 |
| 7,240,251 B2 | * | 7/2007 | Popescu ...................... 714/704 |

FOREIGN PATENT DOCUMENTS

| | | |
|---|---|---|
| DE | 197 28 314 A1 | 1/1999 |
| EP | 1 086 653 A1 | 3/2001 |
| JP | 2-262727 | 10/1990 |

* cited by examiner

*Primary Examiner*—Allen C. Ho
(74) *Attorney, Agent, or Firm*—Oblon, Spivak, McClelland, Maier & Neustadt, P.C.

(57) ABSTRACT

A receiving medium comprising N components is assigned to a channel comprising N components respectively and provided along the circumference around which a rotating frame rotates. At a position facing the receiving medium corresponding to the rotation, the transmission medium of M components ($M \geq 2N$, N represents an integer more than 2) are arranged separately in a line along the circumference of the rotating frame. A signal generation device produces the signal containing data relating to an object obtained by detection of the X-ray detector device. When the transmission medium is rotated according to the carrier signal to face any of the receiving medium, a switching device transmits the signal from the channel to one of the corresponding receiving medium. When the interval between the two adjacent transmission medium passes through the receiving medium, the signal from the same channel may be transmitted to the two adjacent transmission medium.

8 Claims, 14 Drawing Sheets

270 DEGREES ROTATION POSITION

FIG. 9A

| OUTPUT \ TRANSMISSION MEDIUM | 0° | 45° | 90° | 135° | 180° | 225° | 270° | 315° | 360° |
|---|---|---|---|---|---|---|---|---|---|
| 1 a OUTPUT | CH1 | CH1 | CH2* | CH2 | CH2 | CH2 | CH1* | CH1 | CH1 |
| 1 b OUTPUT | CH1* | CH1 | CH1 | CH1 | CH2* | CH2 | CH2 | CH2 | CH1* |
| 1 c OUTPUT | CH2 | CH2 | CH2 | CH2 | CH1 | CH1 | CH1 | CH1 | CH2 |
| 1 d OUTPUT | CH2* | CH2 | CH2 | CH2 | CH1* | CH1 | CH2* | CH1 | CH2* |
| CORRESPONDING FIGURES | FIG.4 | FIG.5 | FIG.6 | - | FIG.7 | - | FIG.8 | - | FIG.4 |

* IS NOT NECESSARILY TO BE SET AND MAY BE INDETERMINATE.
IF THE ABOVE ROTATION ANGLE IS SET TO BE INDETERMINATE OR NOTHING, THE ABOVE CHANNEL IS DEFINED WHEN ROTATION FURTHER PROCEEDS BY THE ABOVE ANGLE + 30 DEGREES.

FIG. 9B

| OUTPUT \ TRANSMISSION MEDIUM | 0° | 45° | 90° | 135° | 180° | 225° | 270° | 315° | 360° |
|---|---|---|---|---|---|---|---|---|---|
| 1 a OUTPUT | CH1 | CH1 | CH2* | CH2* | CH2 | CH2 | CH2 | CH1 | CH1 |
| 1 b OUTPUT | CH2 | CH1 | CH1 | CH1 | CH2* | CH2* | CH2 | CH2 | CH1* |
| 1 c OUTPUT | CH2 | CH2 | CH2 | CH1 | CH1 | CH1 | CH2* | CH2* | CH2 |
| 1 d OUTPUT | CH2* | CH2 | CH2 | CH2 | CH2 | CH1 | CH1 | CH1 | CH2* |

* IS NOT NECESSARILY TO BE SET AND MAY BE INDETERMINATE.

FIG. 11

| OUTPUT / TRANSMISSION MEDIUM | 0° | 30° | 60° | 90° | 120° | 150° | 180° | 210° | 240° | 270° | 300° | 330° | 360° |
|---|---|---|---|---|---|---|---|---|---|---|---|---|---|
| 1e OUTPUT | CH1 | CH1 | CH1 | CH3 | CH3 | CH3 | CH2 | CH2 | CH2 | CH2 | CH1 | CH1 | CH1 |
| 1f OUTPUT | CH1 | CH1 | CH1 | CH1 | CH3 | CH3 | CH3 | CH2 | CH2 | CH2 | CH2 | CH2 | CH1 |
| 1g OUTPUT | CH2 | CH2 | CH2 | CH1 | CH1 | CH1 | CH3 | CH3 | CH3 | CH3 | CH2 | CH2 | CH2 |
| 1h OUTPUT | CH2 | CH2 | CH2 | CH2 | CH1 | CH1 | CH1 | CH1 | CH3 | CH3 | CH3 | CH3 | CH2 |
| 1j OUTPUT | CH3 | CH3 | CH3 | CH2 | CH2 | CH2 | CH2 | CH2 | CH1 | CH1 | CH1 | CH1 | CH3 |
| 1k OUTPUT | CH3 | CH3 | CH3 | CH3 | – | – | – | – | – | – | – | – | CH3 |
| CORRESPONDING FIGURES | FIG.10 | – | – | – | – | – | – | – | – | – | – | – | FIG.10 |

ANGLE OF ROTATION

X-RAY CT APPARATUS AND MEDICAL DATA COMMUNICATION LINK SYSTEM

BACKGROUND OF THE INVENTION

1. Field of the Invention

The field of the present invention relates to a medical data communication link system and an X-ray CT apparatus (or X-ray diagnosis apparatus) which communicate between a rotating frame that takes radiographic image while rotating and a stationary frame that processes the image data received from the rotating frame. In particular, it relates to communication technology relating to the processing of large amounts of data at a high data rate.

2. Description of the Related Art

As shown in FIG. 1(A), the entire constitution of a conventional X-ray CT apparatus is roughly divided into a rotating frame 200, stationary frame 100 (the combination of the rotating frame 200 and the stationary frame 100 is sometimes referred to as gantry) and a console 300. The rotating frame 200 opens to accommodate an object. The rotating frame 200 is constituted such that it can rotate around the object by a rotation-driving device 211. A rotation control device 212 controls the rotation-driving device 211 upon receipt of an instruction from a control device 350 through a coupler 270. During the rotation of the rotating frame 200, an X-ray control device 222 controls the tube voltage, tube current, etc., of an X-ray tube enclosed in an X-ray source 221 upon receipt of the command from control device 350 through the coupler 270. When an X-ray is radiated onto an object by the X-ray source 221, the X-ray transmitted onto the object is received by an X-ray detector 230 and derived by being converted into electric signals for transmission. The X-ray detector 230 is constituted of a plurality of X-ray detector element arrays. A data collector device 240 collects the electric signals from the X-ray detector element arrays. A transmission unit 250 modulates the electric signals from the data collector 240 into a high frequency carrier signal for high data rate transmission to a transmission medium 260. The carrier signal is transmitted to a reception unit 310 through a receiving medium 110 in the stationary frame 100. Using the transmission medium 260 and the receiving medium 110, the carrier signal is transmitted/received by charge coupling. The reception unit 310 demodulates the transmitted carrier signal, and converts the electric signal obtained by demodulation into digital data. Further, the data is constituted of image data relating to the object by a reconstruction processing device 320 and stored in an image memory 330. An image-processing device 340 produces the required image based on the image data from the image memory 330 upon request from the operating device 361 of a user interface 360, and displays the image on a display device 362.

In such X-ray CT apparatus, communication between the rotating frame 200 and the stationary frame 100 is required. Since communication at the side of the coupler 270 mainly consists of a control command from the control device 350 to the rotation control device 212 and X-ray control device 222, the data volume for communication is comparatively small. Meanwhile, in the X-ray detector 230, many X-ray detector element arrays are provided corresponding to the image pixels in order to obtain a precise image finally. For this reason, there is a large amount of communication in the electric signal transfer between the transmission medium 260 and the receiving medium 110. U.S. Pat. No. 5,530,424 employed a charge-coupling system as the communication technology between the rotating frame 200 and the stationary frame 100, and are incorporated herein by reference.

FIG. 2 typically shows the constitution of communication between the transmission unit 250 and reception unit 310 using the charge-coupling system. The electric signal output from the transmission unit 250 is branched into two signals that are equally halved at a branch 250a. The branch 250a consists of an amplifier and a resistor. The branched electric signals are output to a transmission medium 260a and transmission medium 260b, and individually terminated at a terminal 250b. The transmission medium 260a and transmission medium 260b are located in a line around the circumference of the rotating frame 200. The transmission medium 260a and transmission medium 260b extend around the circumference respectively. During rotation, transmission medium 260a and transmission medium 260b are charge-coupled with the receiving medium 110 mounted to the stationary frame 100, and the electric signal is transferred to the receiving medium 110. The receiving medium 110 further transfers the electric signal to the reception unit 310.

In the constitution of FIG. 2, as the length of the transmission line of the route of transmission unit 250—branch 250a—transmission medium 260a—terminal 250b and the length of the transmission line of the route of transmission unit 250—branch 250a—transmission medium 260b—terminal 250b are arranged in the same length, even if the branch 250a or the terminal 250b is hung over the receiving medium 110, the receiving medium 110 can obtain a signal with the same phase (the same time delay) from both the transmission medium 260a and transmission medium 260b due to rotation of the rotating frame 200, thus obtaining a continuous signal without mixing the signals.

Recently, more accurate images are required in a shorter time for medical examinations. Under the circumstances, as shown in FIG. 1(B) for example, with an X-ray detector, the X-ray detector element array has been composed of a plurality of lines and columns with an increasing communication volume in a massive amount. In such a situation, the conventional technology conducts communication by raising the communication frequency (or transfer speed) by several GHz (or GBps). However, because communication occurs through one channel, the above requirements cannot be satisfied.

As one of the methods to respond to such requirements as shown in FIG. 3, the communication system with one channel shown in FIG. 1 may be changed to that of the rotating frame of N layered components shown in FIG. 2, resulting in communication capacity of a plurality of N channels. As clearly shown in FIG. 3, however, this method increases the width of the system, thus having a disadvantage of increasing the space required for installation of the X-ray CT apparatus. Meanwhile, in order to increase the communication capacity, increasing the transmission speed may be considered. However, increasing the transmission speed creates many problems to be solved, such as difficulty in obtaining the same phase (propagation delay) as explained above, and therefore is judged to be impractical.

SUMMARY OF THE INVENTION

The purpose of this embodiment is to provide a medical data communication link system and an X-ray CT apparatus using the system thereof, which are constructed for simultaneous communication through a plurality of channels without increasing the installation space in order to increase the volume of data for simultaneous communication.

In the meantime, the term "channel" is used to indicate a signal transmission line, and a "plurality of channels" or "N channels" means the existence of a transmission line that transmits a plurality of signals or a signal of N components independently, without any relationship to the transmission speed or transmission mode.

In order to achieve the aforementioned purpose, the communication system of the X-ray CT apparatus according to the present embodiment comprises the following compositions.

A signal generation device provided to the rotating frame of an X-ray CT apparatus outputs dividing data into a plurality of channels. A plurality of transmission medium are provided to the rotating frame along the circumference of the rotating frame, while a plurality of receiving medium are provided to the stationary frame such that said receiving medium are provided in intervals along the circumference of the rotating frame. A switching device provided between the signal generation device and the transmission medium assigns the data of a plurality of channels output from the signal generation device to each transmission medium. At the passing of an interval between the two adjacent transmission medium, the switching device switches the data for transmission to the two transmission medium to the data of the same channel. Due to this switching, the signal distributed to each channel containing the data from the X-ray detector can be continuously transmitted to the stationary frame without loss.

It is preferable that, at the passing of the interval between two adjacent transmission medium through the receiving medium, the data in the same channel for transmission to two adjacent transmission medium has mostly the same phase in the two adjacent transmission medium.

According to the above compositions, the medical data from the rotating frame such as the large amount of data detected by the X-ray detector can be divided into a signal of a plurality of channels and the image at the stationary frame can be simultaneously transmitted to the reconstitution process. That is, a large amount of data can be divided in a plurality of channels and transmitted in parallel, enabling high data rate transmission.

BRIEF DESCRIPTION OF THE DRAWINGS

FIG. 9A shows an example of channel output by a transmission medium corresponding to the rotation in the first embodiment.
FIG. 9B shows an example of channel output by a transmission medium corresponding to the rotation in a modification of the first embodiment.

FIG. 11 shows an example of channel output by a transmission medium corresponding to the rotation in the second embodiment.

DETAILED DESCRIPTION OF THE EMBODIMENTS

The following explanation provides embodiments exemplifying 2-channel communication using the medical data communication link system including a "First embodiment" as an example of a 3-channel communication; a "Second embodiment" as a modified example of the first and second embodiments; a "Third embodiment" as a modified example of the first and second embodiments applicable at low data communication speed; and a "Fourth embodiment" and "Embodiment of X-ray CT apparatus" including the medical communication system according to these embodiments.

Figure 1A:
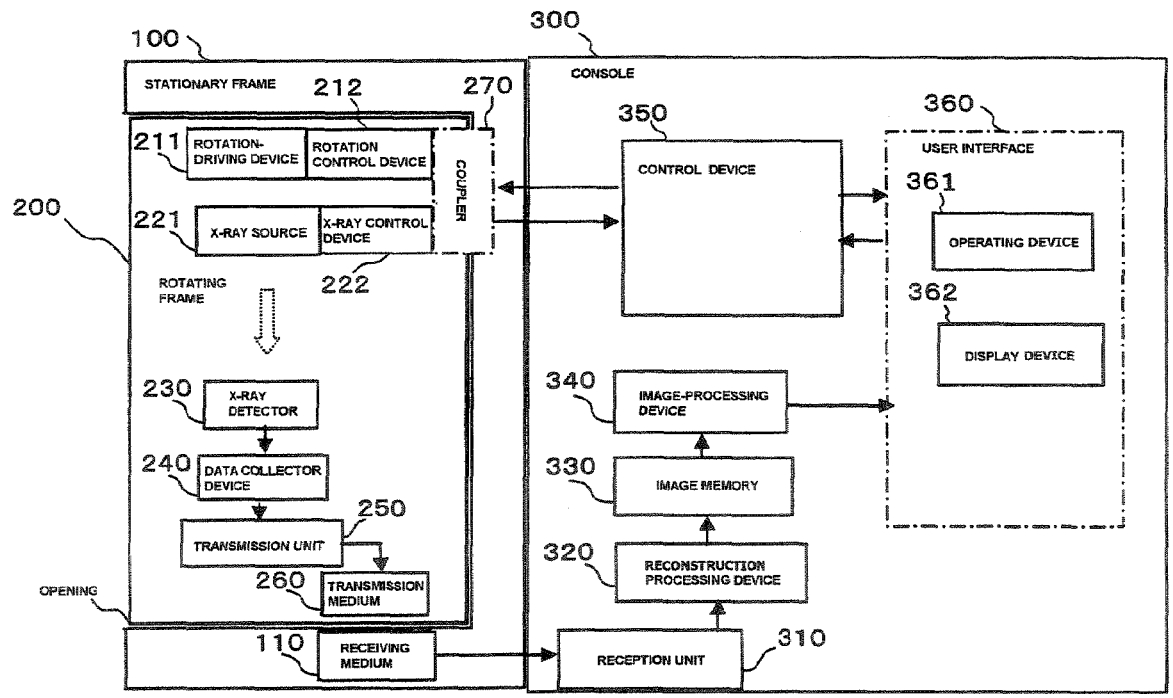
FIG. 1A shows a communication link system of prior art.
Figure 1B:
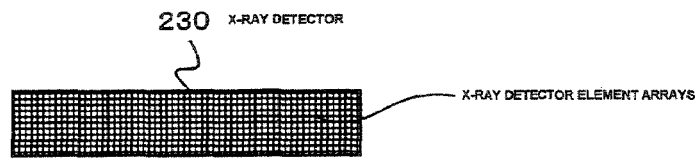
FIG. 1B illustrates a structure of an X-ray detector.
Figure 2:
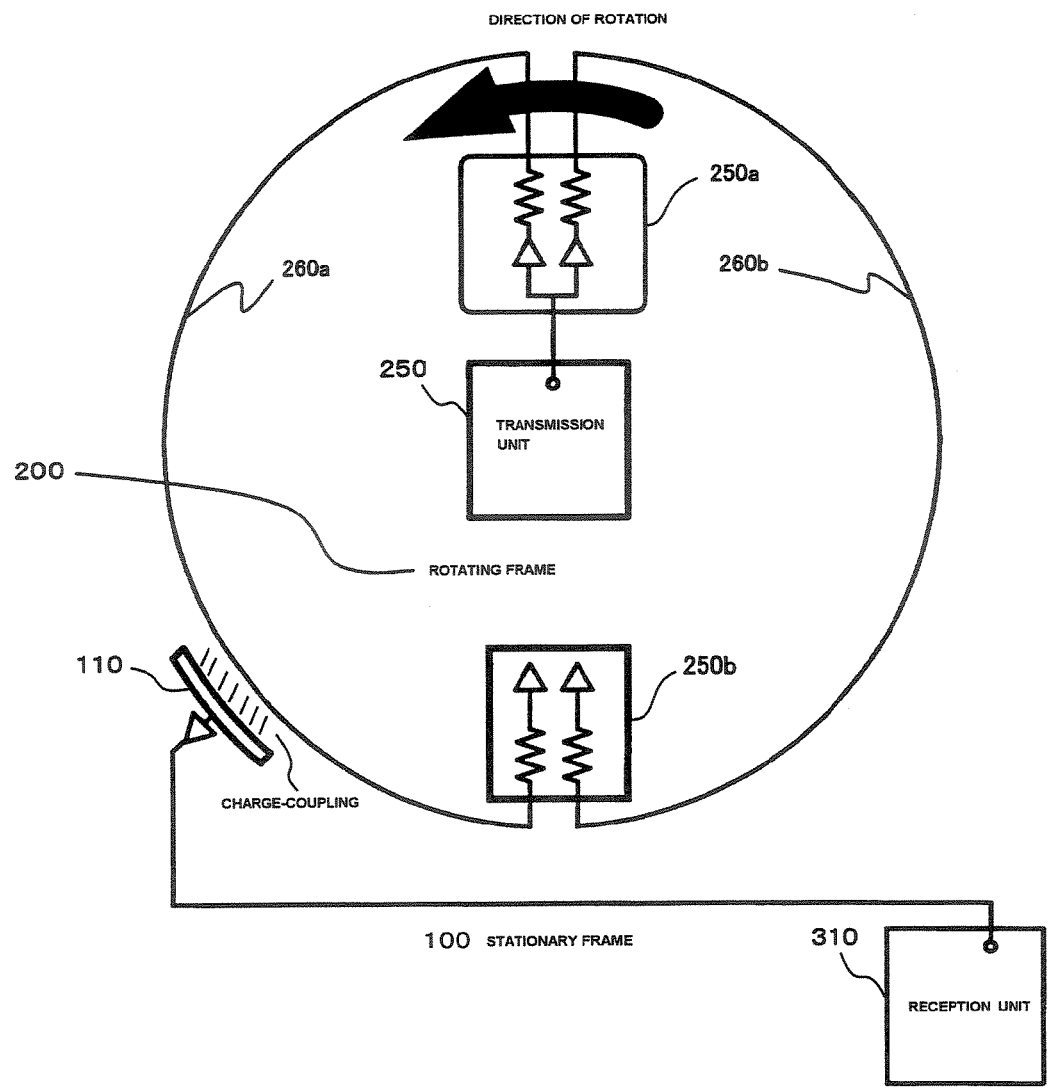
FIG. 2 shows a communication link system of prior art.
Figure 3:
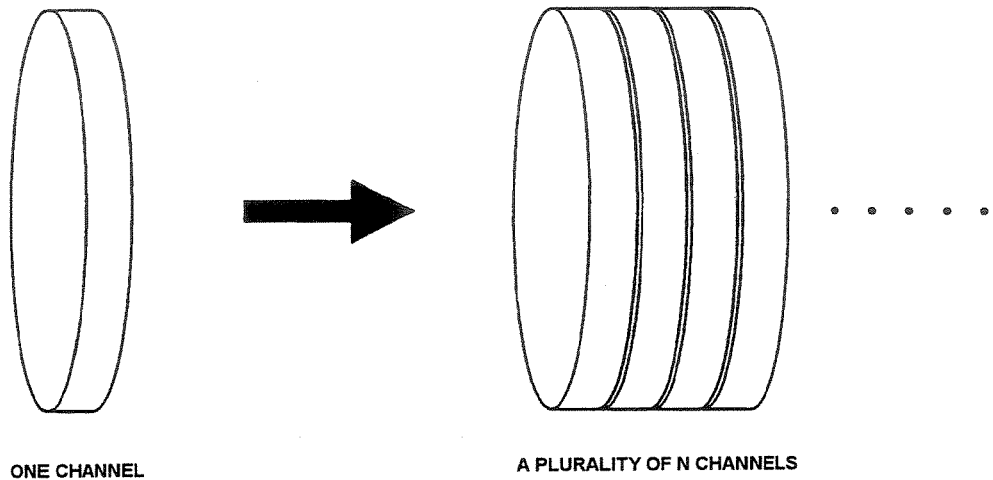
FIG. 3 illustrates a background art relating to this embodiment.
Figure 4:
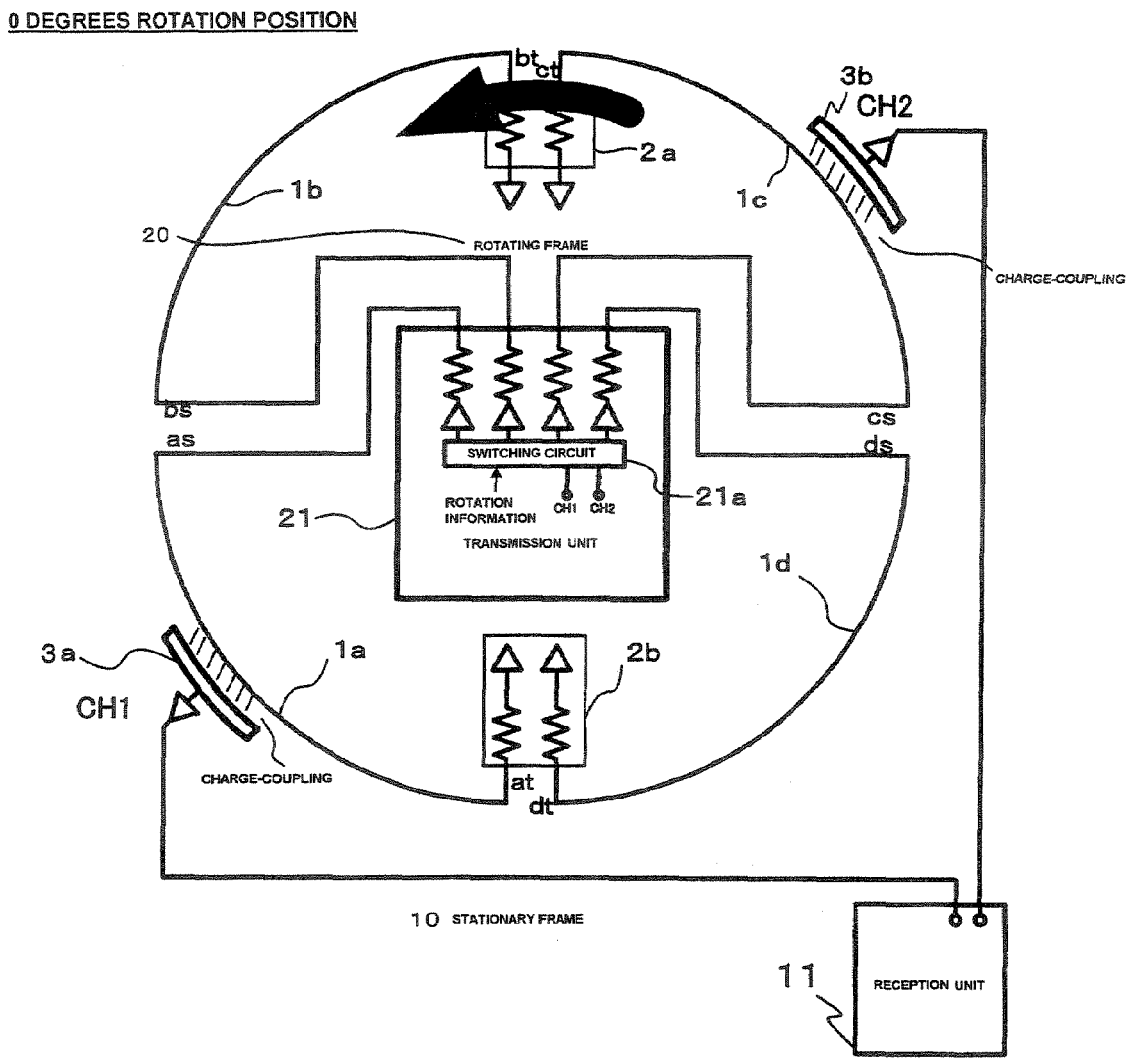
FIG. 4 shows an example of the first embodiment of a medical data communication link system showing an example where the rotating gradient of a rotating frame is 0 degrees.

The structural relationship between the rotating frame 20 and the stationary frame 10 in FIG. 4 is the same as that between the rotating fame 200 and the stationary frame 100 in FIG. 1, and the rotating frame 20 can be housed in an opening of the stationary frame 10. The configuration of communication in all embodiments employs a communication system using charge-coupling or electromagnetic-coupling.

First Embodiment of the Medical Data Communication Link System

FIG. 4 typically shows the constitution of the rotating frame 20 and the stationary frame 10 at the initial stage of rotation (with an angle of rotation of 0 degrees for example). For the rotating frame 20, a transmission medium 1a, transmission medium 1b, transmission medium 1c and transmission medium 1d (hereinafter, "Transmission medium 1" indicates any of the medium individually) are provided in a line in intervals around the circumference of the rotating frame 20. Each transmission medium 1 forms a strip line extending around the circumference. On the stationary frame 10, a receiving medium 3a and a receiving medium 3b (hereinafter "Receiving medium 3" indicates any of the medium individually) are mounted.

The interval between the transmission medium 1 (between ends as—bs, ends bt—ct, ends cs—ds, and ends dt—at in FIG. 4) is shorter than each length of the receiving medium 3a and the receiving medium 3b around the circumference. This is so in order to simultaneously receive the same signal from the transmission medium 1a and the transmission medium 1b, and to smoothly shift the transfer from the transmission medium 1a to the receiving medium 3a to that from the transmission medium 1b to the receiving medium 3a, when the interval between the ends as and bs, for example, are rotated to face the receiving medium 3a (refer to FIG. 5). The same can be applied to the transfer of a signal to the receiving medium 3b. When the receiving medium 3 crosses over the two adjacent transmission medium 1, the receiving medium 3 receives the same signal (data) from the two transmission medium 1

The length around the circumference of any transmission medium 1 is the same. The ends of all transmission medium 1 (ends as, bs, cs and ds in FIG. 4) are connected to the transmission unit 21, and the other ends (ends at, bt, ct and dt in FIG. 4) are individually terminated at the terminal 2a or terminal 2b with a specified resistance. Further, the facing ends of the transmission medium 1 located adjacent around the circumference are connected to the transmission unit 21, or connected to the same terminal 2a or terminal 2b. The upstream ends in relation to the signal from the transmission unit 21 (ends as and bs, or cs and ds, for example) are located facing each other, and the downstream ends (ends bt and ct, or ends dt and at) are located facing each other and connected to the terminal 2a or terminal 2b.

The length of the transmission line from the transmission unit 21 to the end of each transmission medium 1 (ends a-s, b-s, c-s, and d-s in FIG. 4) is substantially the same. The length of the transmission line between the transmission medium 1 is also substantially the same. Therefore, when the same signal (signal with same transmission speed) is transmitted to each transmission medium 1, the phase of the signal (propagation delay) at the ends as and bs is at least substantially the same, the phase of the signal (propagation delay) at the ends bt and ct is the same, the phase of the signal (propagation delay) at the ends cs and ds is substantially the same, and further, the phase of the signal (propagation delay) at the ends dt and at is substantially the same.

Figure 5:
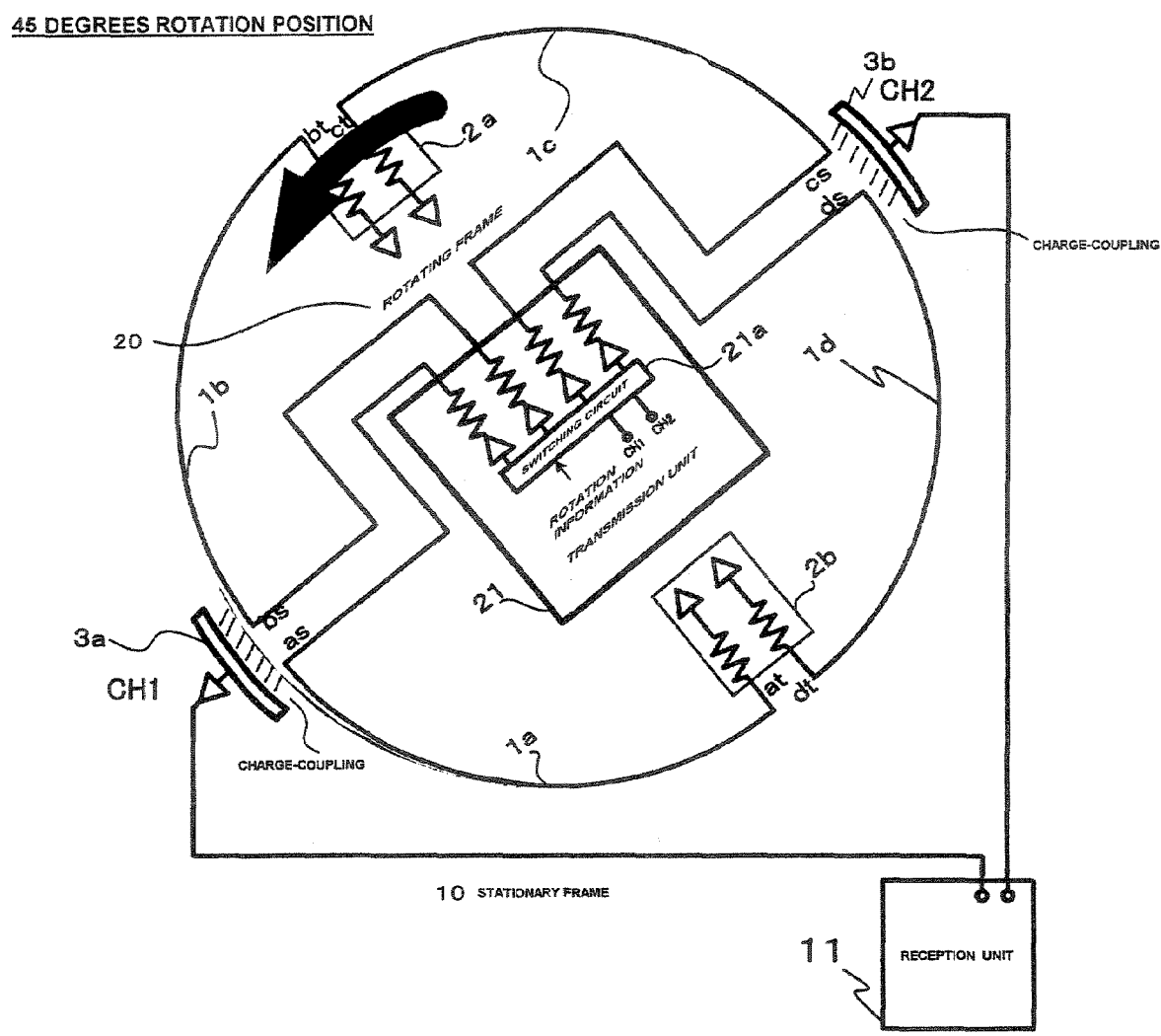
FIG. 5 shows an example of the rotating frame rotated 45 degree in relation to the case shown in FIG. 4.

This is, for example, to allow reception of the same signal with the same phase from the transmission medium 1a and the transmission medium 1b when the portion between the ends as and bs are rotated to face the receiving medium 3a (refer to FIG. 5). The term "substantially the same" above means within an allowable range wherein data error is not generated. When the constitution includes a means (variable delay element, phase shifting device, variable line element) to make the phase the same between the transmission unit 21 to each transmission medium 1, the length of the line may be different. Therefore, "length of the transmission line" above does not indicate a dimensional length but indicates an effective length of the line including phase (delay).

The two receiving medium 3a, 3b are provided at about same distance from the rotating center of the rotating frame 20. The intervals around the circumference are more than the length of one transmission medium 1, and less than the length of three transmission medium in a line around the circumference (The following explains the arrangement in contrast to the rotating center as shown in FIG. 4.). The receiving medium 3a and 3b are provided to receive the signal from channel CH1 and channel CH2. Using the transmission medium 1 and the receiving medium 3, the signal is transmitted/received by charge-coupling or electromagnetic-coupling. When the electromagnetic-coupling system is employed, the receiving medium 3 has a coil shape.

Each signal of channel CH1 and channel CH2 is amplified and received by the reception unit 11. The receiving medium 3 and transmission medium 1 to which the signal from channel CH1 and channel CH2 are transferred are electrically connected by so-called charge-coupling. The length of the intervals between receiving medium 3 around the circumference is longer than the length of one transmission medium 1.

The transmission unit 21 of the rotating frame 20 is provided with the signal generation device (not shown in the figure) to generate the signal of channel CH1, and the signal generation device (not shown in the figure) to generate the signal of channel CH2. The transmission unit 21 is equipped with a switching circuit 21a (switching device), which receives the signals from channel CH1 and channel CH2 individually, switches the signals based on the rotation information such as rotation angle, and transmits them to each transmission medium 1 through an amplifier or resistor. Each signal generation device receives data from the data-generating device 240 in FIG. 14 described later, and cooperatively converts into the desired transmission speed for signal generation. The rotation information may be information on the rotation angle when the rotating frame 20 is controlled by a rotation control device 212 described later or information on the rotation angle measured by a rotation sensor 400.

Next, the switching action is explained based in FIGS. 4-8 showing the position of rotation of the rotating frame 20 and FIG. 9(A) showing switching by the switching circuit 21a.

FIG. 4 shows an angle of rotation of 0, wherein the switching circuit 21a outputs the signal from channel CH1 to the transmission medium 1a and the transmission medium 1b following in the direction of rotation, and outputs the signal from the channel CH 2 to the transmission medium 1c and the following transmission medium 1d as shown in FIG. 9(A). Switching is performed to transmit the same signal by the two transmission medium 1 nearing the one receiving medium 3. (The same is applicable to any embodiments.) Various timing can be applied for the timing of switching to the same signal according to the degree of proximity to the receiving medium 3. For example, for the transmission medium 1b and transmission medium 1d with an angle of rotation of 0 degrees, switching may be performed according to the signal at 0 degrees shown in FIG. 9(A), and no signal or other signals may be acceptable. (This state is called "indefinite." The most delayed timing for transmitting the same signal to the two transmission medium 1 is explained below for a 45-degree rotation angle.)

FIG. 5 indicates an angle of rotation of 45 degrees, wherein the switching circuit 21a outputs the signal from channel CH1 to the transmission medium 1a and the transmission medium 1b following in the direction of rotation as shown in FIG. 9(A), and outputs the signal from the channel CH 2 to the transmission medium 1c and the following transmission medium 1d. In this case, it is desirable to transmit the signal from channel CH1 to the transmission medium 1b at least when the end as of the transmission medium 1a contact the receiving medium 3a, and to transmit the signal from channel CH2 to the transmission medium 1d when the end cs of the transmission medium 1c contacts the receiving medium 3b. For example, although it depends on the length of the receiving medium 3, if the position immediately before contact between the end as of the transmission medium 1a and the receiving medium 3a stays within an angle of rotation of 0 and 30 degrees, the switching circuit 21a transmits the signal from channel CH1 at 30 degrees (rotation angle 0 degrees+30 degrees shown in FIG. 9(A)) to the transmission medium 1b, and transmits the signal from channel CH2 to the transmission medium 1d. It is desirable to establish the state at 0 degrees+30 degrees from the infinite state. It is necessary to determine the signal for transmission to the transmission medium 1b when the end as of the transmission medium 1a is located facing the receiving medium 3a and the signal for transmission to the transmission medium 1c when the end Cs of the transmission medium 1c faces the receiving medium 3b at the latest. When the receiving medium 3 crosses over the adjacent two transmission medium 1, the switching circuit 21a outputs the signal from the same channel to the two transmission medium 1.

The infinite period above may be a period when the transmission medium 1b is shifting between a position facing the receiving medium 3b and a position facing the receiving medium 3a (when the transmission medium 1d is shifting between the position facing the receiving medium 3a and that facing the receiving medium 3b). This is the period in which the signals are to be transmitted from the channels to the transmission medium 1b and transmission medium 1d. In order to create this period, the distance along the circumference of the receiving medium 3 is set to be longer than the length of the transmission medium 1, and the number of the transmission medium 1 is set to more than 2 times the number of receiving medium 3.

Figure 6:
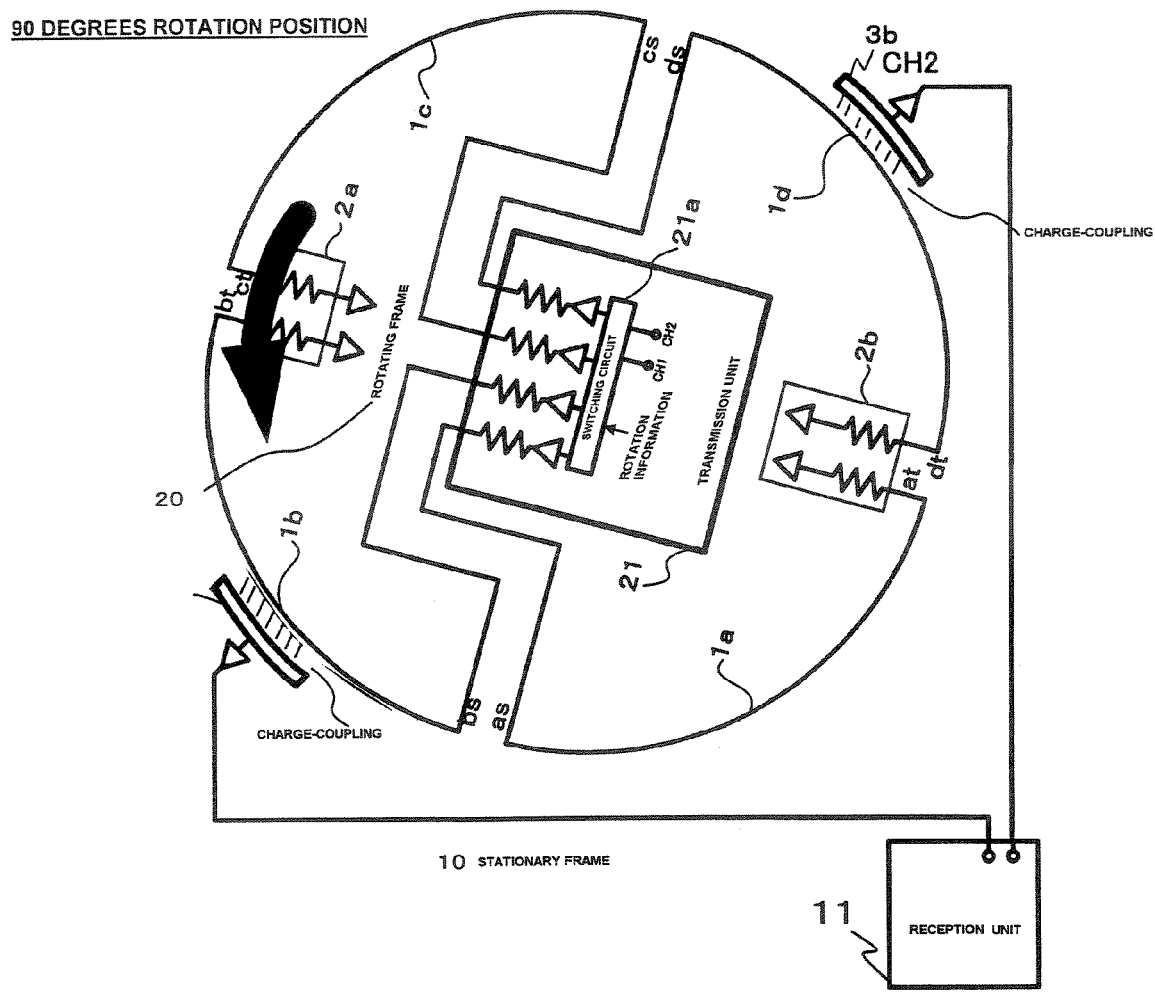
FIG. 6 shows an example of the rotating frame rotated 90 degrees in relation to the case shown in FIG. 4.

FIG. 6 shows an angle of rotation of 90 degrees, wherein the switching circuit 21a outputs the signal from channel CH1 to the transmission medium 1b and the transmission medium 1c following in the direction of rotation as shown in FIG. 9(A), and outputs the signal from the channel CH2 to the transmission medium 1d and the following transmission medium 1a. However, for the transmission medium 1c and transmission medium la, switching may be performed according to the signal at 90 degrees shown in FIG. 9(A), or no signal or other signals may be acceptable (indefinite).

For an angle of rotation of 135 degrees, not shown in the figures, the switching circuit 21a outputs the signal from channel CH1 to the transmission medium 1b and the transmission medium 1c following in the direction of rotation as shown in FIG. 9(A), and outputs the signal from the channel CH2 to the transmission medium 1d and the following transmission medium 1a. In this case, it is preferable to transmit the signal from channel CH1 to the transmission medium 1c and to transmit the signal from channel CH2 to the transmission medium 1a at least before the end bt of the transmission medium 1b contacts the receiving medium 3a, and before the end dt of the transmission medium 1d contacts the receiving medium 3b (for example, at the angle of rotation 90 degrees+30 degrees=120 degrees shown in FIG. 9(A)) (assuming the infinite state at an angle rotation of 90 degrees).

Figure 7:
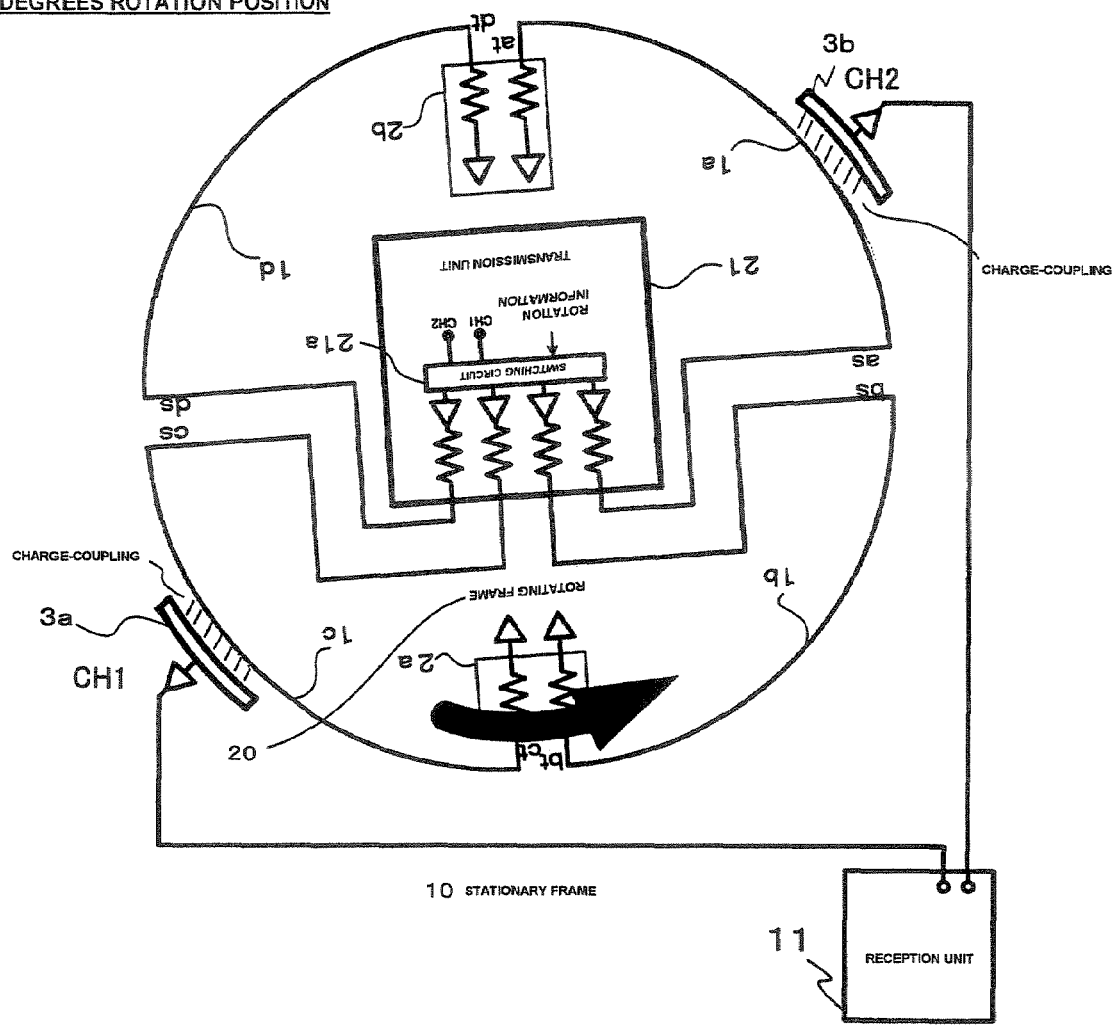
FIG. 7 shows an example of the rotating frame rotated 180 degrees in relation to the case shown in FIG. 4.

FIG. 7 indicates an angle of rotation of 180 degrees, where the switching circuit 21a outputs the signal from channel CH1 to the transmission medium 1c and the transmission medium 1d following in the direction of rotation as shown in FIG. 9(A), and outputs the signal from the channel CH2 to the transmission medium 1a and the following transmission medium 1b. However, for the transmission medium 1d and transmission medium 1b, switching may be performed according to the signal at 180 degrees shown in FIG. 9(A), and no signal or other signals may also be acceptable (indefinite).

For an angle of rotation of 225 degrees, not shown in the figures, the switching circuit 21a outputs the signal from channel CH1 to the transmission medium 1c and the transmission medium 1d following in the direction of rotation as shown in FIG. 9(A), and outputs the signal from the channel CH2 to the transmission medium 1a and the following transmission medium 1b. In this case, it is preferred to transmit the signal from channel CH1 to the transmission medium 1d and transmit the signal from channel CH2 to the transmission medium 1b before the end cs of the transmission medium 1c contacts at least the receiving medium 3a, and until the end as of the transmission medium 1a contacts the receiving medium 3b (at rotation angle 180 degrees+30 degrees=210 degrees in FIG. 9(A), for example) (assuming an infinite state at an angle of rotation of 180 degrees).

Figure 8:
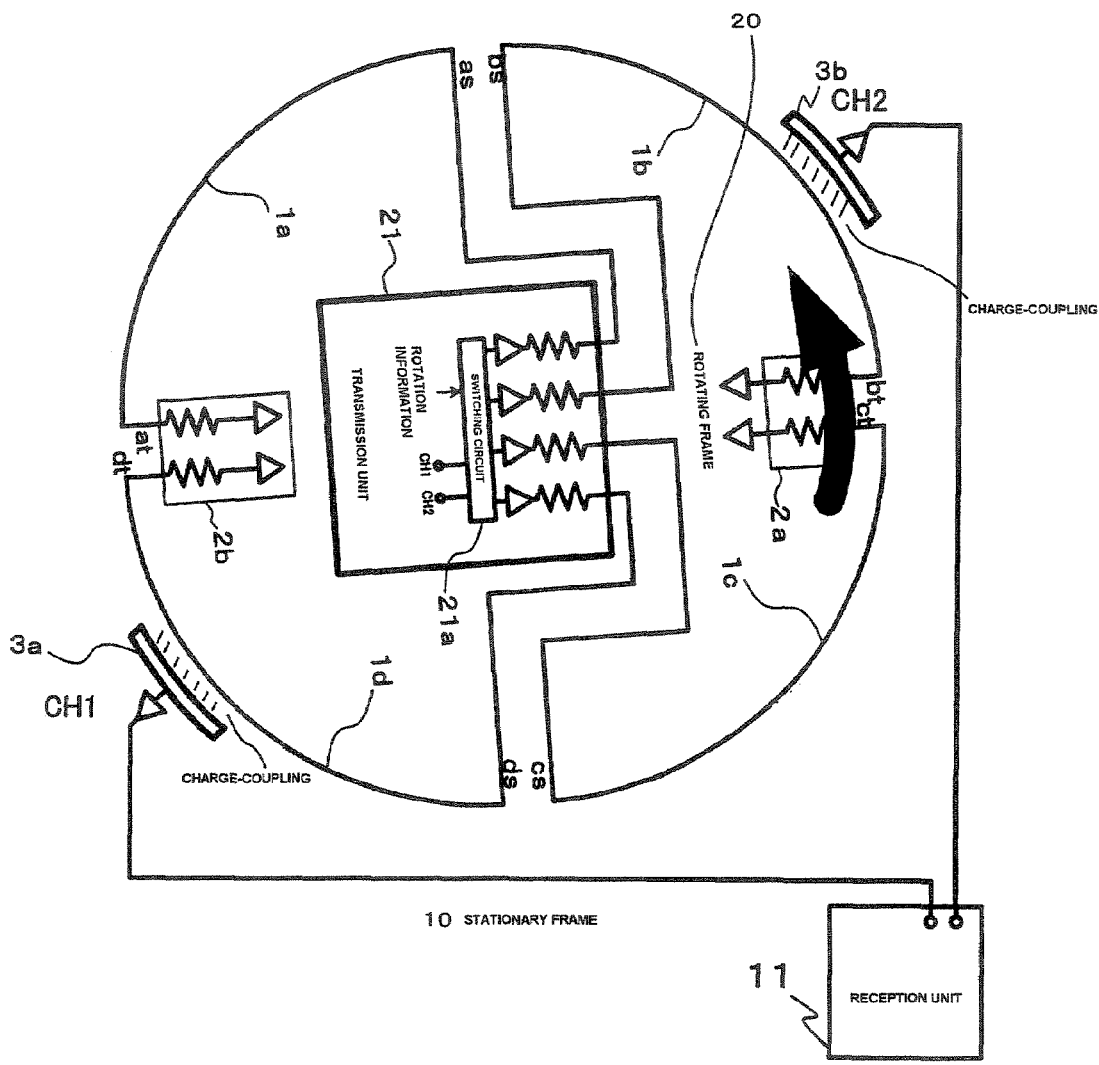
FIG. 8 shows an example of the rotating frame rotated 270 degrees in relation to the case shown in the figure.

FIG. 8 indicates an angle of rotation of 270 degrees, wherein the switching circuit 21a outputs the signal from channel CH1 to the transmission medium 1d and the transmission medium 1a following in the direction of rotation as shown in FIG. 9(A), and outputs the signal from the channel CH2 to the transmission medium 1b and the following transmission medium 1c. However, for the transmission medium 1a and transmission medium 1c, switching may be performed according to the signal at 270 degrees shown in FIG. 9(A), and no signal or other signals may also be acceptable (indefinite).

For an angle of rotation of 315 degrees, not shown in the figures, the switching circuit 21a outputs the signal from channel CH1 to the transmission medium 1d and the transmission medium 1a following in the direction of rotation as shown in FIG. 9(A), and outputs the signal from the channel CH2 to the transmission medium 1b and the following transmission medium 1c. In this case, it is desirable to transmit the signal from channel CH1 to the transmission medium 1a and transmit the signal of channel CH2 to the transmission medium 1c before the end dt of the transmission medium 1d contacts at least the receiving medium 3a, and until the end bt of the transmission medium 1b contacts the receiving medium 3b (at an angle of rotation of 270 degrees+30 degrees=300 degrees in FIG. 9(A), for example). The case of an angle of rotation of 360 degrees is the same as that in FIG. 4, and the rotation hereafter is repeated for switching following the conditions shown in FIG. 9(A).

Since the transmission medium 1 and the receiving medium 3 are arranged and constituted as above, and the switching circuit 21a is constituted so as to allow switching of the signal for transmission to the transmission medium 1 corresponding to the rotation of the rotating frame 20, the signal of the two channels can be continuously transmitted without generating an error.

Modified Example of the First Embodiment

As explained above, as in FIG. 4, the receiving medium 3a and the receiving medium 3b are not necessarily positioned symmetrically to the rotating axis, while the receiving medium 3b may be located to provide 135 degrees between the receiving medium 3b and the receiving medium 3a in the direction of rotation, and 225 degrees between the receiving medium 3a and the receiving medium 3b in the direction of rotation as well. In this case, the switching circuit 22a may be switched to constitute the conditions shown in FIG. 9(B) in correspondence to the rotation angle. Meantime, the meaning of "infinite" in FIG. 9(B) is the same as that in FIG. 9(A). Not limited to this example, operation is possible provided that the distance between the two receiving medium 3 remains within the length of one to three transmission medium.

Second Embodiment of the Communication System

Figure 10:
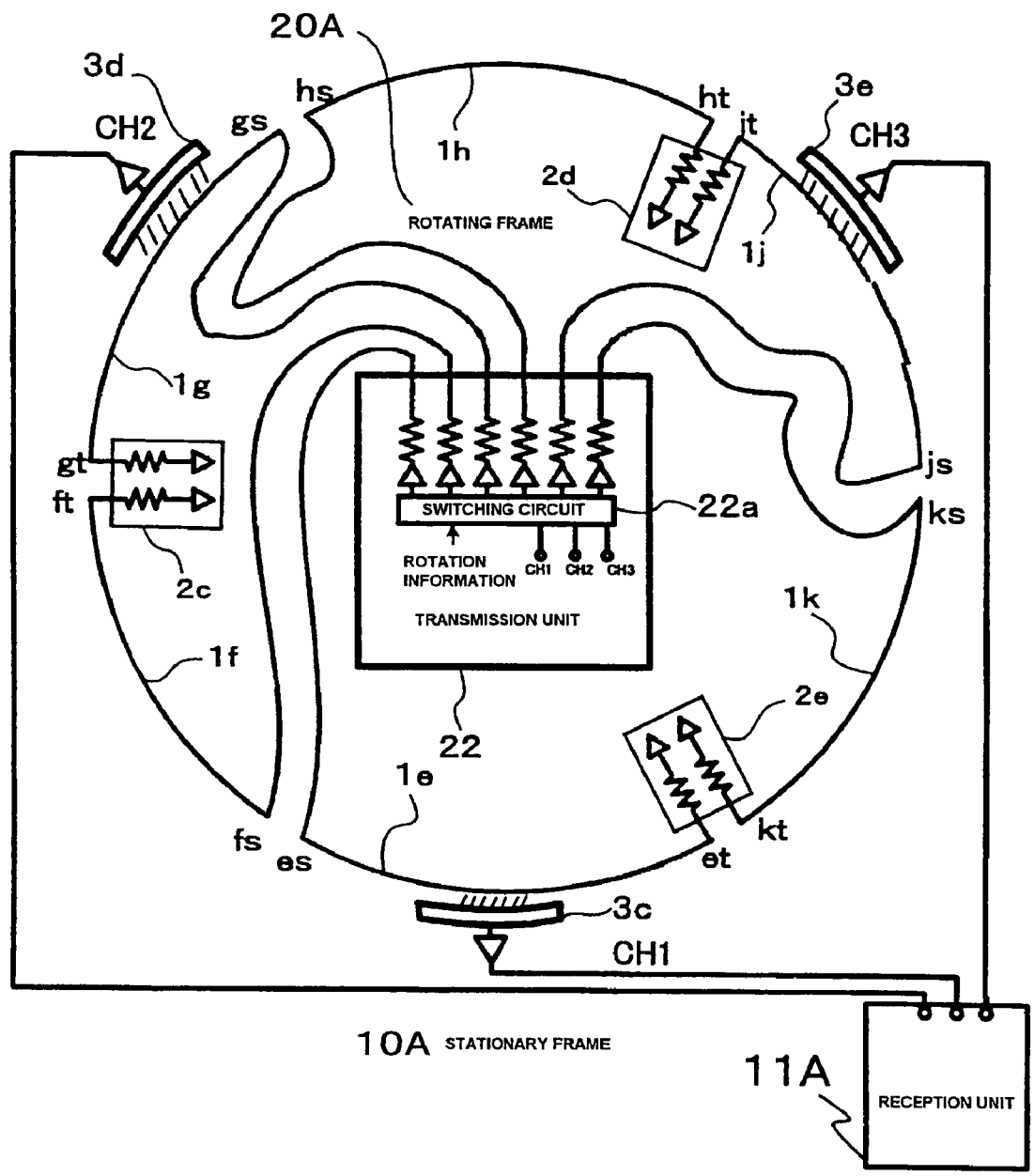
FIG. 10 shows a functional block of the second embodiment of the medical data communication link system.

FIGS. 10 and 11 show an example expanding up to three channels. The conditions for this expansion include a number of receiving medium 3 more than N components and the number of transmission medium 1 more than 2N components relative to the channel of several N components.

FIG. 10 shows three-channel communication, wherein the number was increased proportionate to the number in the composition/action of the first embodiment for two-channel communication. Accordingly, the dimensions, arrangement, and action in response to the rotation angle become smaller according to the number of channels; however, the technological concept is the same, for which a brief explanation is given below.

FIG. 10 shows the typical constitution of a rotating frame 20A with a rotation angle of 0 degrees and the stationary frame 10A. At the rotating frame 20A, the 6 transmission medium 1e-1k (excluding 1i) (hereinafter, "Transmission medium 1" indicates any of the medium individually) are provided in intervals in a line around the circumference. The distance between medium (the distance between ends es and fs, ends ft and gt, ends gs and hs, ends ht and jt, ends js and ks, and ends kt and et) is at least shorter than the length around the circumference of the receiving medium 3c, receiving medium 3d or receiving medium 3e mounted on the side of the stationary frame 10A (hereinafter, "Receiving medium 3" indicates any of the medium individually). The intervals between receiving medium 3 around the circumference are set to be longer than the transmission medium 1.

In addition, the length of all transmission medium 1 around the circumference is set to be equal. At any transmission medium 1, the one end (ends es, fs, gs, hs, js, ks in FIG. 10) is connected to the transmission unit 22, and the other end (ends et, ft, gt, ht, jt, kt in FIG. 10) is terminated at the terminal 2c, terminal 2d or terminal 2e (hereinafter, "Terminal" indicates an individual terminal) with a specified resistance. Further, at each transmission medium 1, the terminals of the adjacent facing transmission medium 1 are connected to the transmission unit 22 or to the terminal.

The length of the transmission line from the transmission unit 22 to the end of each transmission medium 1 (the ends es, fs, gs, hs, js, ks in FIG. 4) is substantially equal. The length of the transmission line between the transmission medium 1 is also substantially equal. Therefore, the phase between the terminals of each transmission medium is set to be equal when the same signal (signal with same transmission speed) is transmitted to each transmission medium.

For the stationary frame 10A, three receiving medium 3c, 3d, 3e are provided at a substantially same distance from the rotation center of the rotating frame and separated in intervals of greater length than the length of one transmission medium 1 (not limiting to symmetrical positioning, although FIG. 10 shows symmetrical positioning against the rotation center). The receiving medium 3c, receiving medium 3d and receiving medium 3e of the transmission medium 1 (hereinafter, "Receiving medium 3" indicates each receiving medium 3c, 3d, 3e individually) are provided to receive the signal from channel CH1, channel CH2 and channel CH3 respectively.

The transmission unit 22 of the rotating frame 20A is provided with a signal generation device (not shown in the figures) that generates the signal of the three channels, CH1, CH2 and CH3 individually, and the switching circuit 22a switches the signal from each channel in response to the rotation information, such as the rotation angle, as shown in FIG. 11, for transmission to each transmission medium 1. FIG. 11 shows an example of the signal from the channels output by each transmission medium 1 in a case wherein switching is controlled according to rotation angle with the receiving medium 3 positioned symmetrically as shown in FIG. 10.

Since the action of the second embodiment in FIG. 10 is based on the same concept as the first embodiment, a detailed explanation of FIG. 11 is omitted. At the switching circuit 22a, the receiving medium 3 crosses over between the ends of the transmission medium 1 for each 60 degrees of rotation angle as shown in FIG. 11 (30 degrees, 90 degrees, 150 degrees, 210 degrees, and 270 degrees in FIG. 11), replacing the transmission medium 1 transferring the signal to the receiving medium 3 at this time. Therefore, it is important not to interrupt the signal due to this replacement. Although the indefinite period is not shown in FIG. 11, the transmission medium 1 between the receiving medium 3 has an undefined period and it can be switched (defined) to output the same signal as the channel signal of the preceding transmission medium 1 until the indefinite state enters a position facing the next receiving medium 3.

Third Embodiment of the Communication System

Figure 12:
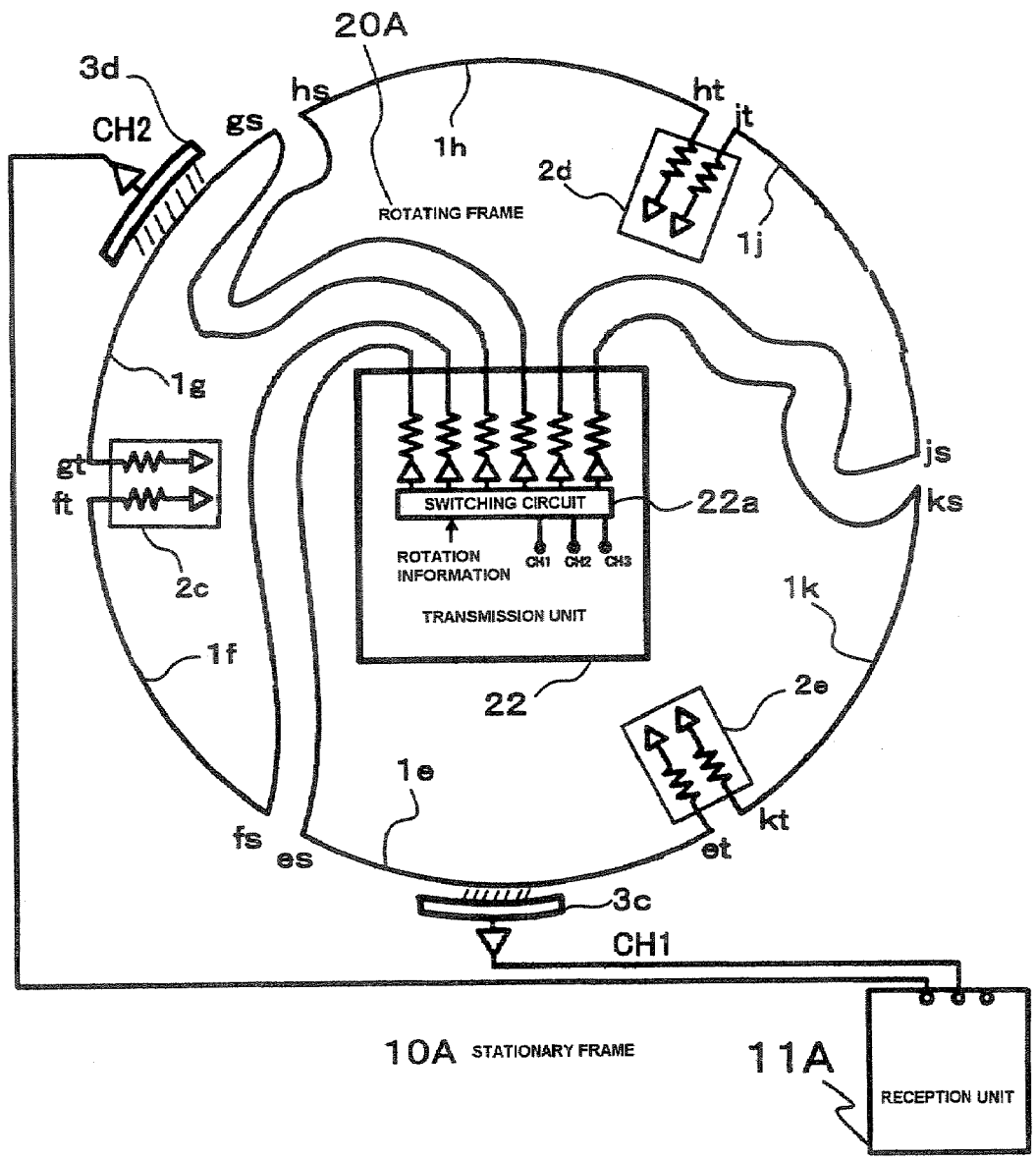
FIG. 12 shows a functional block of the third embodiment of the medical data communication link system.

FIG. 12 provides an example of an embodiment enabling three-channel communication shown in FIG. 10, wherein the receiving medium 3e is excluded to modify into two-channel communication. The third embodiment shows that N channel communication is possible if the number of transmission medium 1 counts for more than M components exceeding 2N components. FIG. 12 is an example wherein the number of transmission medium 1 is counted as 6 components (M=6) with two channels (N=2). M=5, 7, etc. is also possible with N=2.

In FIG. 12, the switching circuit 22a may be switched in the same way as in FIG. 11. Only the signal from channel CH3 is not transferred. When a signal generated in the signal generation of channel CH3 by the transmission unit 22 will be unused, the signal from CH3 shown in FIG. 11 will be eliminated, but this is acceptable; however, the signal from CH3 shown in FIG. 11 may equal the channel signal from the adjacent transmission medium 1 following in the direction of rotation.

In the first embodiment and the second embodiment of said communication system an explanation was provided for a case in which the transmission medium 1 and the receiving medium 3 are located symmetrically against the rotating frame 20 (20A). The operational efficiency of the resources (transmission medium 1, etc.) related to the rotation angle employing symmetrical arrangement is better than non-symmetrical arrangement (the third embodiment, for example).

Fourth Embodiment of the Communication System

Figure 13:
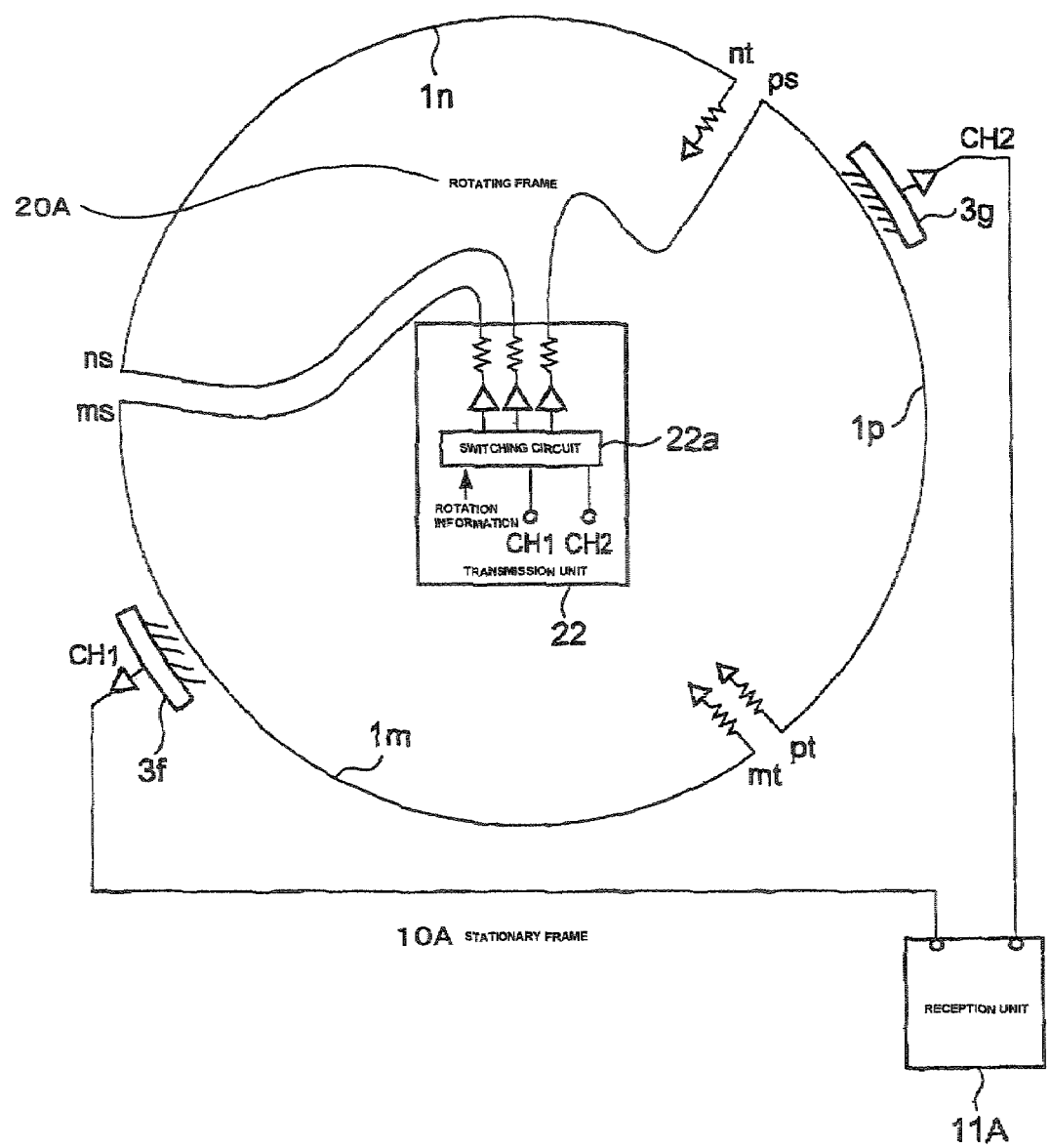
FIG. 13 shows a functional block of the fourth embodiment of the medical data communication link system.

FIG. 13 shows a modified example allowing data communication among multi-channels even when the number of the transmission medium 1 does not exceed 2N components under the specified conditions. This modified example of this embodiment can be applied when the data transmission speed of the transmission unit 22 and the reception unit 11A is slow, such as a speed under the order of GHz, or when the diameter of the rotating frame 20A is small.

As shown in FIG. 13, in the communication system of this embodiment, the transmission medium 1m, the transmission medium 1n and the transmission medium 1p are assigned to the receiving medium 3f and receiving medium 3g. While the receiving medium 3 counts for 2 components, the transmission medium 1 counts for 3 components. Each of the transmission medium 1 expand in the range of 120 degrees, and the receiving medium 3f and receiving medium 3g are arranged symmetrical to the rotation center. The receiving medium 3f and receiving medium 3g is further separated by the length of one receiving medium 1, and the same transmission medium 1 does not pass through simultaneously.

The end ms of the transmission medium 1m faces the end ns of the transmission medium 1n, and both ends are on the starting side in relation to the signal flow. While the end mt of the transmission medium 1m faces the end pt of the transmission medium 1p and both ends are on the terminating side in relation to the signal flow. Therefore, if a signal from the same channel is fed to the transmission medium 1m and transmission medium 1n, a signal of the same phase will be fed to the ends ms and ns. And if a signal from the same channel is fed to the transmission medium 1m and transmission medium 1p, a signal of the same phase will be fed to the ends mt and pt.

While the end nt of the transmission medium 1n faces the end ps of the transmission medium 1p, and the end nt of the transmission medium 1n is on the terminating side, and the end ps of the transmission medium 1p is on the starting side in relation to the signal flow, the phase of the signal will deviate at the ends nt and ps if a signal of the same channel is fed to the transmission medium 1n and the transmission medium 1p. However, when the data transmission speed of the signal to be output by the transmission unit 22 is slow, or when the diameter of the rotating frame 20A is small, the deviation of the phase will be the same in an allowable range wherein data error will not be generated, and the data transmission/reception will have no problem when the ends nt and ps passing through the receiving medium 3f, 3g.

Embodiment of the X-ray CT Apparatus

Figure 14:
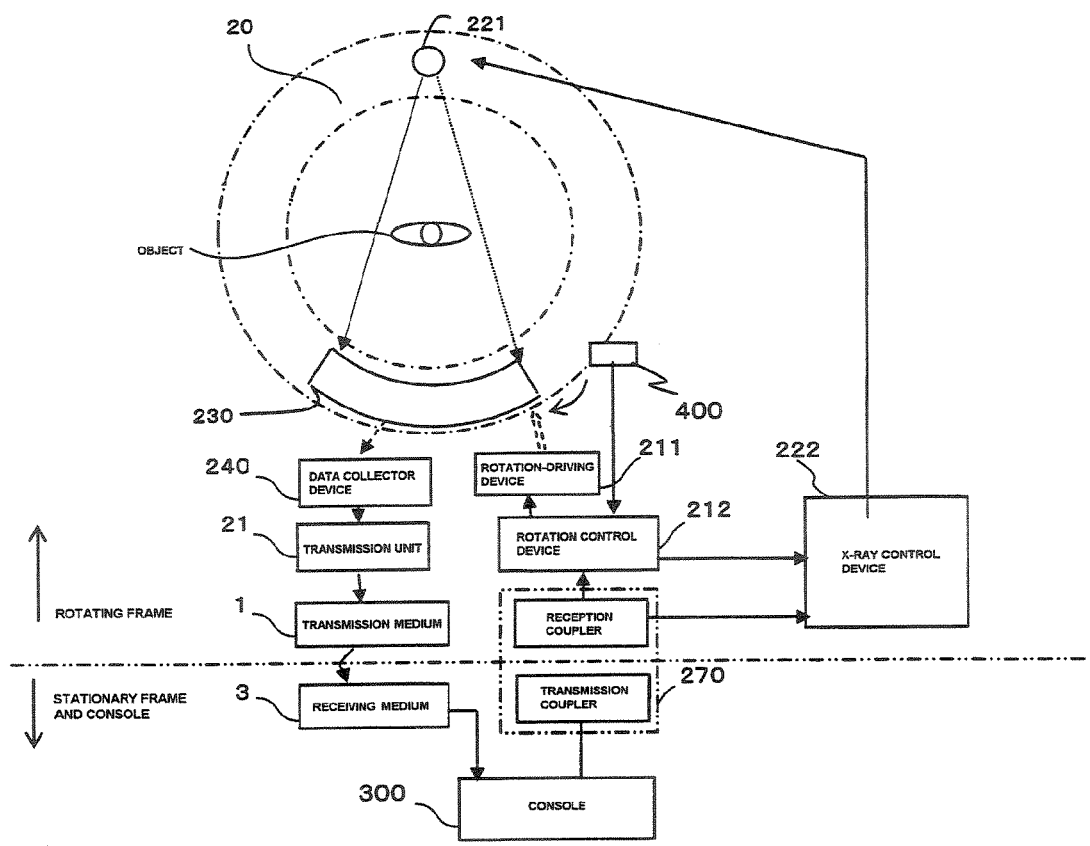
FIG. 14 shows an example of a functional block of an X-ray CT apparatus.

FIG. 14 represents the functional block diagram of an embodiment relating to the X-ray CT apparatus. Although the terminology is different from that in FIG. 1, the position/structure of the stationary frame, rotating frame and console are the same as in FIG. 1. In addition, the symbols indicate the same functions as in FIG. 1.

The difference between FIG. 14 and FIG. 1 is that the rotating frame 200, transmission unit 250, transmission medium 260 and receiving medium 110 are replaced with the rotating frame 20 (or 20A), transmission unit 21 (or 22), transmission medium 1a, 1b, 1c and 1d (or 1e, 1f, 1g, 1h, 1j, and 1k), and receiving medium 3a and 3b (or 3c, 3d and 3e) in FIGS. 4-8, FIG. 10 and FIG. 12. As the above components are employed in the medical communication system explained in the embodiments 1-3, their explanation is omitted.

Therefore, the action is the same as that shown in FIG. 1 as a whole, and the action of the medical communication system follows the embodiments 1-3.

In the meantime, the X-ray CT apparatus in which the receiving medium 3 are located symmetrically in relation to the rotating axis of the rotating frame 20 is composed of the constitution below.

An X-ray CT apparatus having a rotating frame 20 comprising an X-ray radiation device 221 and an X-ray detector 230 that detects radiated X-rays, as well as an opening (not shown) that accommodates the rotating frame 20, and a stationary frame (not shown) having a receiving medium 3 of N components fixed and arranged around the circumference of a concentric circle centered around the rotating axis of the rotating frame 20 at the same intervals in order to receive signals (N represents an integer more than 2) from at least N channels, wherein the rotating frame 20 comprises a signal generation device that outputs the signal from N channels differing from each other at least based on the output of the X-ray detector 230, a transmission medium 1 of 2N components in a line of a same length arranged to form another concentric circle in parallel to said concentric circle, and a switching device that receives the signal of N components from the signal generation device, then switches said signal from the two channels by the specified rotation angle of the rotating frame 20 (360 degrees/2N) to transmit to each transmission medium 1, and transmits the signal from different channels of the two transmission medium, thereby enabling communication via charge-coupling of the signal from the channel of N components between the transmission medium 1 and the receiving medium 3.

Further, the switching device switches each signal for the specified rotation angle (360 degrees/2N) such that the signal from the same channel can be transmitted by the transmission medium 1 rotated to face each receiving medium 3 by rotation of the rotating frame 20 and the transmission medium 1 that follows in the direction of rotation.

In the above case, the X-ray CT apparatus was equipped with a plurality of transmission medium 1 located around the circumference of the rotating frame 20, and a plurality of receiving medium 3 located in a line. However, the timing of channel switching by the switching circuit 21a should be switched for each rotation of 360/2N times, and the timing will be more complicated as the number of channels increases. Accordingly, a limitation will be applied in practical use for the plurality of transmission medium 1 and plurality of receiving medium 3 provided in a line around the circumference of the rotating frame 20.

Figure 15:
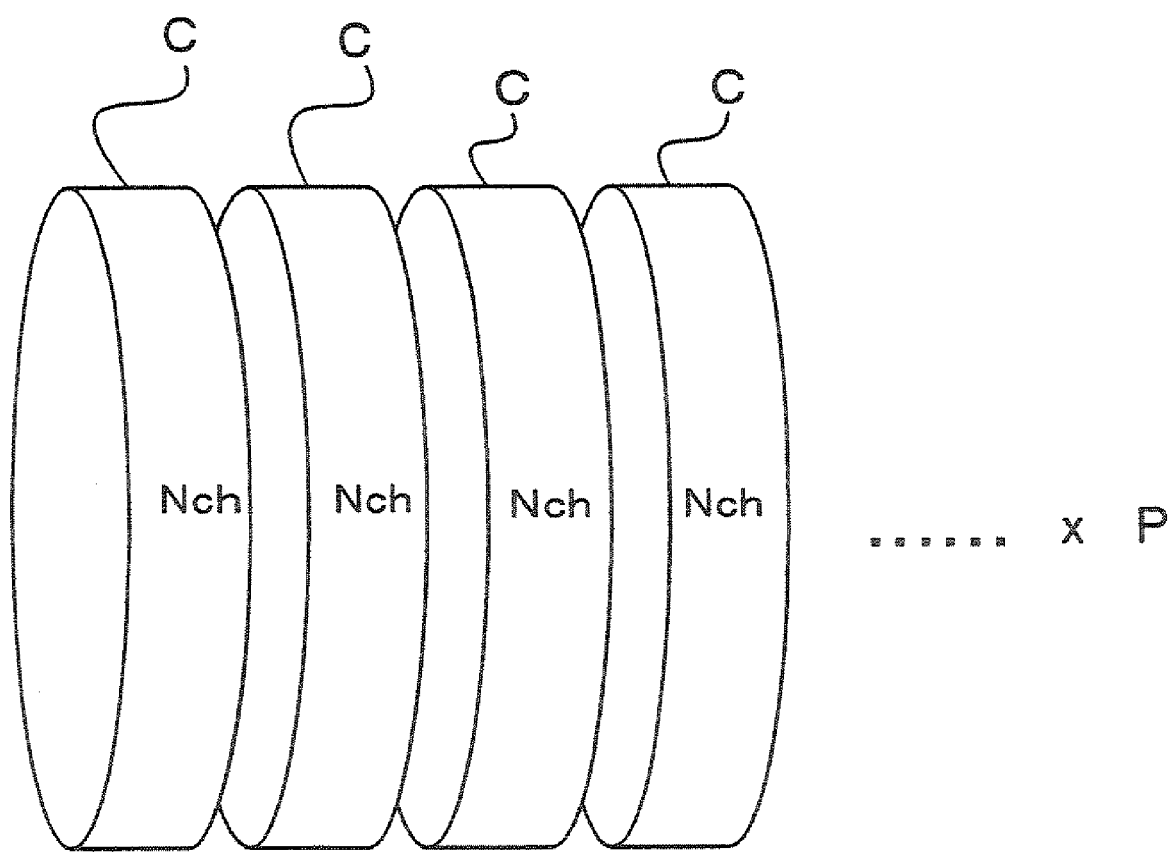
FIG. 15 shows a modified example of the data communication link system to be provided to X-ray CT apparatus.

Under the circumstances, as shown in FIG. 15, a combination C of the plurality of transmission medium 1 and plurality of receiving medium 3 arranged in a line may be provided in multiple lines in the direction of the rotation axis of the rotating frame 20. Assuming that the medical data of N channels can be received in one line, the medical data can be dividing into channels of N×P components to be transmitted/received when employing a combination of the plurality of transmission medium 1 and plurality of receiving medium 3. By defining the type of channels for transmission/reception per line, switching may be made within the range of specified channels.

For example, a combination of four transmission medium 1 and two receiving medium 3 is provided in two lines on the rotating frame 20. The signal generation device divides medical data into 1-4 channels, and the switching circuit 21 a always assigns channels 1-2 to the first line, and channels 3-4 to the second line. Each transmission medium 1 provided to the first line transmits the data from channels 1 and 2 being switched in response to the rotation angle of the rotating frame 20, and each transmission medium 1 provided to the second line transmits the data from channels 3 and 4 being switched in response to the rotation angle of the rotating frame 20.

As explained above, since the application of the medical data communication link system to an X-ray CT apparatus can transmit a large amount of radiographic images quickly, the detailed images can be reconstructed for output (display).

Meantime, the technological scope of this invention includes various modifications apparent to those skilled in the art and is not limited to the embodiments explained above.

What is claimed is:

1. An X-ray CT apparatus having a rotating frame, a stationary frame, and a data communication link system for data communication between said rotating frame and said stationary frame, wherein said data communication link system comprises:

a signal generation device located in said rotating frame, which divides the data into a plurality of channels for output;

a plurality of receiving mediums corresponding to a plurality of channels, which are provided in said stationary frame around said rotating frame;

a plurality of transmission mediums provided separately along the circumference of said rotating frame; and a switching device assigning to each transmission medium, the data from said plurality of channels output from said signal generation device, and switching the data to be transmitted to two adjacent transmission mediums into data of a same channel when an interval between the two adjacent transmission mediums passes nearby a receiving medium, wherein said plurality of transmission mediums and said plurality of receiving mediums conduct data communication by charge-coupling or electromagnetic-coupling; and N receiving mediums are provided so as to correspond with N channels, and said transmission mediums are provided as 2N components.

2. The X-ray CT apparatus according to claim 1, wherein said rotating frame comprises an X-ray tube that radiates X-rays and an X-ray detector that detects X-rays transmitted onto an object;

said stationary frame comprises a data processing circuit to process the data output by said X-ray detector; and said data communication link system divides the data output by said X-ray detector into a plurality of channels for transmission to said data processing circuit.

3. The X-ray CT apparatus according to claim 1, wherein said switching device switches the data to be transmitted to a transmission medium in accordance with the rotating angle of said rotating frame.

4. The X-ray CT apparatus according to claim 1, wherein transmission lines are provided between said signal generation device and said each transmission medium and have the same line length for effective transmission; and said receiving medium passing through the interval between the two adjacent transmission medium receives data of the substantially same phase.

5. The X-ray CT apparatus according to claim 1, wherein any ends facing said adjacent two transmission mediums are arranged to be located upstream or downstream of the data flow to be transmitted.

6. The X-ray CT apparatus according to claim 1, wherein said data communication link system is provided with a plurality of combinations of said plurality of receiving mediums and said plurality of transmission mediums in parallel in the axial direction of said rotating frame.

7. An X-ray CT apparatus equipped with a rotating frame, a stationary frame, and a data communication link system for data communication between said rotating frame and said stationary frame, comprising:

an X-ray tube provided at said rotating frame to radiate X-rays;

an X-ray detector provided at said rotating frame to detect the X-rays transmitted onto an object;

a signal generation device provided at said rotating frame to divide data output by said X-ray detector into N channels for output;

a transmission medium of 2N components provided separately in a line along the circumference of said rotating frame, any of which have the same line shape and length of one transmission line;

a switching device provided to said rotating frame to assign said N channels to each transmission medium upon receipt of each data divided into N channels from said signal generation device; and a receiving medium of N components provided to said stationary frame located along the circumference of said rotating frame that receives data by charge-coupling or electromagnetic coupling, wherein said switching device transmits data to each transmission medium via the switching of the 2 channels per rotation of 360/2N degrees of said rotating frame, then transmits the data from the different channels for each 2 transmission mediums, and when an interval between two adjacent transmission mediums passes near a receiving medium, switches the data to be transmitted to the two adjacent transmission mediums to a same channel, wherein said plurality of transmission mediums and said plurality of receiving mediums conduct data communication by charge-coupling or electromagnetic-coupling; and N receiving mediums are provided so as to correspond with N channels, and said transmission mediums are provided as 2N components.

8. A data communication link system for a medical diagnosis apparatus that relays data communication between a rotating frame and a stationary frame, comprising:

a plurality of receiving mediums provided to said stationary frame around said rotating frame and corresponding to a plurality of channels;

a plurality of transmission mediums provided separately along the circumference of said rotating frame; and a switching device that assigns the plurality of channels to each transmission medium, and switches the data to be transmitted to two adjacent transmission mediums to a same channel when an interval between the two adjacent transmission mediums passes near a receiving medium, wherein said plurality of transmission mediums and said plurality of receiving mediums conduct data communication by charge-coupling or electromagnetic-coupling; and N receiving mediums are provided so as to correspond with N channels, and said transmission mediums are provided as 2N components.

* * * * *

UNITED STATES PATENT AND TRADEMARK OFFICE
CERTIFICATE OF CORRECTION

PATENT NO. : 7,502,438 B2
APPLICATION NO. : 11/623991
DATED : March 10, 2009
INVENTOR(S) : Nakagawa et al.

It is certified that error appears in the above-identified patent and that said Letters Patent is hereby corrected as shown below:

On the title page, Item (73), the Assignee information is incorrect. Item (73) should read:

-- (73)　　Assignee:　　Kabushiki Kaisha Toshiba, Tokyo (JP);
　　　　　　　　　　　　Toshiba Medical Systems Corporation,
　　　　　　　　　　　　Otawara-shi (JP) --

Signed and Sealed this

Twelfth Day of May, 2009

JOHN DOLL
*Acting Director of the United States Patent and Trademark Office*